United States Patent [19]
Davitt

[11] Patent Number: 6,041,445
[45] Date of Patent: Mar. 28, 2000

[54] ADAPTIVE UNDERGARMENT

[76] Inventor: Patricia Davitt, 341 Reed St., Manchester, N.H. 03104

[21] Appl. No.: 09/061,715

[22] Filed: Apr. 17, 1998

[51] Int. Cl.[7] .................................................. A41B 9/00
[52] U.S. Cl. ........................... 2/400; 2/406; 2/408; 2/247
[58] Field of Search .................. 2/69, 69.5, 114, 2/400, 401, 402, 403, 404, 405, 406, 407, 408, 247, 248, 249, 250, 251, 252, 253

[56] References Cited

U.S. PATENT DOCUMENTS

| | | | |
|---|---|---|---|
| 1,866,428 | 7/1932 | Smith | 2/247 |
| 3,137,862 | 6/1964 | Mizerak . | |
| 3,840,901 | 10/1974 | Eyster | 2/247 |
| 4,533,355 | 8/1985 | Fair . | |
| 4,578,062 | 3/1986 | Schneider . | |
| 4,852,188 | 8/1989 | Marsh et al. . | |
| 4,888,006 | 12/1989 | Beaupied . | |
| 5,135,520 | 8/1992 | Beaupied . | |
| 5,165,115 | 11/1992 | Stanislaw . | |
| 5,172,430 | 12/1992 | Lerma-Solis | 2/400 |
| 5,241,710 | 9/1993 | Lockhart | 2/406 |

*Primary Examiner*—Gloria M. Hale
*Attorney, Agent, or Firm*—Robert R. Deleault, Esq.; Mesmer Law Offices, P.A.

[57] ABSTRACT

An adaptive undergarment is provided for persons with specialized urological needs. The adaptive undergarment provides an elongate pocket for storing specialized urological articles. The elongate pocket is located preferably in a parallel spaced relationship with the waistband of the user's undergarment. The adaptive undergarment may have an additional pocket elsewhere on the undergarment for storing items such as antibacterial wipes. Each pocket is open at one edge to receive and provide access to the stored items. Any type of undergarment conforming to any user's specialized urological needs is adaptable into this adaptive undergarment.

20 Claims, 4 Drawing Sheets

ADAPTIVE UNDERGARMENT

BACKGROUND OF THE INVENTION

1. Field of the Invention

The present invention relates to adaptive clothing. Particularly, the present invention relates to adaptive clothing for use by persons suffering from certain diseases, medical conditions or physical handicaps. More particularly, the present invention relates to adaptive clothing worn as undergarments for holding medical catheters where persons having various medical conditions require clean intermittent catheterization for removal of body fluid wastes.

2. Description of the Prior Art

Adaptive clothing has been designed and made in the past especially for persons suffering from certain diseases, medical conditions and physical handicaps. Generally, this type of adaptive clothing addresses specific needs of a patient. For instance, various garments have been devised for holding, storing, supporting, and receiving certain indwelling catheters. These garments for indwelling catheters are for use with intravenous catheters or ostomy catheters.

Intravenous catheters may be implanted inside the patient and may remain implanted for months at a time. It was important to provide a means of supporting the sterile sponge at the site where the catheter becomes exposed from the patient's body as well as supporting the protruding tube and coupling. Without the support, the tube and coupling would hang loosely down on the patient. The prior art discloses various devices for holding the exposed intravenous tubing.

Generally, ostomy patients have a stoma attached to the body. The stoma is surgically constructed through which urine or feces will pass. The size and location of the stoma varies from patient to patient as a result of the surgical procedure followed. These patients typically rely on the use of an ostomy appliance for the collection and discharge of urine and/or feces discharged through the stoma. Ostomy undergarments have been devised to provide support of the ostomy appliance for the comfort of the user.

The undergarment devices in the prior art have all been designed for patients requiring the implantation of medical appliances or devices on a long-term basis. The problem that these prior art devices have identified and try to solve is to properly support and hold the associated medical appliances connected to the patient. Additional goals of these prior art devices are the patient's comfort and the ability to hide or to minimize the apparent protrusions in the outer garments worn by these patients.

U.S. Pat. No. 5,135,520 (1992, D. Beaupied) teaches an ostomy garment having a pair of crisscross pocket forming panels configured to lie behind an ostomy device. The crisscross overlapping arrangement of the pocket forming panels forms an elongated slot above the crossover region. The panels are releasably joined together at their top portions over a range of relative positions, including space apart and overlapping conditions, so as to provide a measure of adjustment to the tension provided in support of the device. The panels also provide an improved degree of surrounding of the ostomy device flange when the ostomy device is emplaced relatively low on the user's abdomen.

U.S. Pat. No. 4,888,006 (1989, D. Beaupied) teaches an ostomy undergarment having front, back and crotch panels, waist and leg bands stitched together to construct a typical panty or undergarment. The garment incorporates a retaining pocket and closure device. The retaining pocket has an opening defined by a crisscross arrangement which surrounds the connected flanges of an appliance and contains the appliance pouch apart from the user's abdomen.

U.S. Pat. No. 4,533,355 (1985, M. Fair) teaches a loose-fitting garment for individuals wearing an ostomy appliance with an encircling band which contacts the body above the stoma. The garment has a downwardly extending fabric which covers the torso. This fabric has a large vertical opening therein and a pocket on the exterior covering a portion of the opening. The appliance fitted to the stoma extends through the opening and rests in the pocket. A cover flap is provided to shield the appliance from view.

U.S. Pat. No. 4,578,062 (1986, P. Schneider) teaches a re-usable intravenous catheter holder in the shape of a cut-off tank top body garment. The garment is fitted securely around the patient's chest by an elastic band around the base of the garment. The holder supports a catheter tube and coupling which protrudes from the patient's chest. The garment also provides a means whereby the shoulder strap of the garment may be opened to allow access to the catheter without removal of the holder.

These prior art devices, however, fail to address the needs and concerns of another class of persons. This class of persons are people that require artificial means for discharging body fluids such as urine on a short-term basis and only when required. These people do not require long-term implantation of catheters. They need only to implant and use the catheter each time they need to empty their bladders. An example of such a person is someone with Spina Bifida. Heretofore, there did not exist any adaptive clothing that met the needs of these persons, persons capable of self-catheterization. A person who performs self-catheterization is required to carry around a clean catheter in the user's pocket, pocketbook, purse, handbag, etc. Cleanliness and privacy are problems that are associated with intermittent catheterization. A person required to perform intermittent catheterization must do so several times a day.

What is needed is an adaptive clothing undergarment that is inexpensive to manufacture and easy to clean. What is further needed is an undergarment that is specially designed for people who must undergo clean intermittent catheterization in order to empty their bladder. What is still further needed is an undergarment that holds the catheter in a secure place and keeps the catheter protected. Finally what is needed is an undergarment that allows the wearer to conveniently store the catheter before and after use, that has another holder for storing sanitary wipes for cleaning the catheter before or after each use, and that allows the user the ability to perform intermittent self-catheterization in the privacy of a bathroom stall without anyone else knowing of the user's need for intermittent self-catheterization.

SUMMARY OF THE INVENTION

It is therefore an object of the present invention to provide an undergarment which has a private storage pocket for people in need of storing items related to their specialized urological needs. It is a further object of this invention to make this storage pocket convenient for the user to access. Another object of the present invention is to provide an undergarment with a storage pocket that will always be near the user when the adaptive clothing device is worn. Another object of the present invention is to provide an undergarment with a storage pocket that alleviates the need to carry items necessary for specialized urology needs in pockets, purses, plastic bags, school bags, specialized belts, etc. where they are easily lost, forgotten, or inconvenient. Another object of the present invention is to provide an undergarment with a storage pocket that is easy to clean. It is yet another object of the present invention is to provide an undergarment with a secure storage pocket that protects the stored item and minimizes the possibility of their loss. A further object of the present invention is to provide an adaptive clothing undergarment that is inexpensive to manufacture. Yet another object of the present invention is to provide an undergarment that minimizes the embarrassment felt by persons needing to perform self-catheterization by providing an adaptive undergarment that will be indistinguishable from undergarments without the adaptation when worn normally under their outerwear.

The present invention achieves these and other objectives by providing a pocket which can be used to store items necessary for a person's specialized urological needs. The pocket can be pre-attached to an undergarment. Existing undergarments can also be altered to provide this pocket. The pocket has an opening at one of the edges to allow insertion and removal of items such as a catheter but is closed at the other three edges in order to provide a secure place where the items cannot easily fall out and become lost. The pocket may be equipped with a flap that covers the open edge or with a fastener such as buttons, snaps or hook and loop fasteners that may be used to close the open edge of the pocket and provide greater security against loss of the stored items. Furthermore, this opening can be placed in a way that accommodates the wearer of the undergarment whether they are left or right handed. By having a pocket within which the items that they need can be stored, a person wearing the catheter undergarment always has the specialized item that they need in a secure, convenient place.

The catheter undergarment also allows a person with specialized urological needs to retain a certain amount of privacy regarding their need for catheterization or other procedure. While away from one's residence, a user can place a clean catheter into the pocket of the undergarment, out of sight of the general public. The catheter does not need to be placed in a purse, pocketbook, backpack, bag, pockets of outerwear or otherwise need to be actively carried. When needed, the hidden urological device can be privately removed from its pocket for use in a bathroom stall or other suitable area. The pocket may be placed horizontally just below the waistband of a wearer's regular undergarment where it will attract little or no attention and be effectively hidden from sight under the user's regular clothing. This will reduce any potential embarrassment for persons in need of performing self-catheterization by minimizing the possibility that others will find out about the user's need for self-catheterization from merely observing the wearer of the undergarment.

Any type of existing undergarment may be altered to provide the pocket. Alternatively, people may buy garments that are prefabricated with the pocket. This is possible for undergarments such as briefs, boxer shorts, body shirts, or long underwear manufactured for men, women, boys and girls. The inclusion of a pocket or pockets on an undergarment during the manufacturing process can be done inexpensively. A great convenience is realized by wearers of catheter undergarments because it allows them to always have the items they need the most in a handy location on a garment that they are already accustomed to purchasing and wearing.

Another benefit of the present invention is that it also allows for ease of cleaning in that it may be laundered along with other items of clothing. There is no need for the user to launder his catheter undergarment any differently than they previously laundered their unaltered undergarments. No specialized instructions or laundering will be necessary.

Another embodiment of the present invention also includes a second pocket that may be used to store items such as small antibacterial wipes. These wipes can be used to clean both the user's hands and the catheter itself both prior to and after catheterization. Having these antibacterial wipes in such a convenient place may increase their use and subsequently decrease the risk of infection for the user which is always a concern of people with specialized urological needs. Placement of this additional pocket on the catheter undergarment will also be effectively hidden from sight underneath the user's outer garments.

The catheter undergarment of the present invention is comprised of an undergarment that includes a front and a back side, a top and a bottom. There is a waistband located at the top of the undergarment and a crotch separating two leg openings at the bottom of the undergarment. The back of the undergarment is connected to the front forming undergarments such as briefs, boxer shorts, panties, long underwear, bodyshirts, etc. There is also an elongate pocket attached to the undergarment just below the waistband. This pocket has one open edge designed to receive and allow access to the wearer of the catheter undergarment for easy retrieval of a stored item such as a catheter when necessary. The other edges of the pocket are closed or sealed in order to increase the security of the stored items. An additional pocket may be attached to the undergarment at another location on the fabric body. This pocket also has one open edge while all other edges are closed and can be used to store other useful items, preferably small antibacterial wipes. This second pocket may have a covering flap or a fastening mechanism to close the top side. This would prevent items stored in this second pocket from falling out of the second pocket during movement.

The present invention may also be attached to existing undergarments using a kit that includes some or all of these components including an attachable elongate pocket, a securing device, a second pocket, a covering flap, and a closing fastener for either pocket. This kit would allow persons in need of performing clean intermittent self-catheterization to alter the undergarments they already own to embody the present invention. The attachable elongate pocket included in the kit would be adapted to the user's urological or other specialized need. The securing device could be a type of glue, heat activated adhesive, a strip of hook and loop fasteners, thread, string, buttons, snaps, epoxy, or any other device capable of securably attaching the elongate pocket to the fabric body of the undergarment. For kits utilizing a type of glue or epoxy as the securing device, the glue or epoxy may be pre-applied to the edges of each attachable elongate pocket. One preferred embodiment of the present invention includes at least one attachable elongate pocket that has heat activated adhesive disposed on all of the edges except one. The adhesive on the edges of the pocket could then be activated by a heating device such as an iron to secure the pocket onto the desired location on the undergarment. This pocket could then be further secured by stitching the edges of the pocket which are adhered to the undergarment. The closing fastener could take on any one of a number of different forms including buttons, snaps, hook and loop fasteners, or any other fastener capable of providing increased security against loss of the pocket contents. The kit may also include other pockets adapted to hold other specialized items once attached to the fabric body of the undergarment. Any of the pockets in the kit may have a covering flap which would be placed over the open edge of the pocket and would reduce the possibility of losing items out of the open edge of the pocket when pulled down over the open edge.

To manufacture the present invention, manufacturers would produce undergarments in the exact same way that they are produced currently. However, they would undergo at least one additional step. This additional step would be to create at least one pocket by attaching additional pieces of fabric of sufficient size to hold specialized devices to the body of the undergarment. This piece of fabric that is attached may have a closing flap over the edge that is left open or it may be equipped with a closing fastener to help prevent loss of items out of the open edge of the pocket.

To use the present invention, one would don the catheter undergarment in exactly the same way they don the undergarments that they currently wear. For example, the wearer may hold the fabric body of the catheter undergarment and align the front and the back, effectively positioning the leg openings for insertion of the wearer's legs. Next they would insert their legs through the proper leg openings and pull the undergarment up until the waistband was properly situated around their waist. If they had not done so already, they would insert a catheter or other specialized item into the pocket for storage. If the catheter undergarment was equipped with additional pockets, other useful items could be placed in them at that time. The wearer could then finish getting dressed in their routine fashion. Anytime the wearer of the catheter undergarment needed to perform clean, intermittent self-catheterization, they could enter a bathroom stall, remove their outerwear, retrieve their catheter from the pocket, clean their hands and catheter with their stored antibacterial wipes, perform the self-catheterization, once again clean their hands and catheter with their stored antibacterial wipes, return the catheter to its pocket, and get redressed. This can all be accomplished privately without informing others of the need to perform clean, intermittent self-catheterization or exposing the items necessary for self-catheterization. In this way, the present invention allows for the user to perform self-catheterization with high levels of cleanliness and privacy.

Additional advantages and embodiments of the present invention will be set forth in part in the detailed description which follows, and in part will be apparent from the description, or may be learned by practice of the invention. It is understood that the foregoing general description and the following detailed description are exemplary and explanatory and are intended to provide further explanation of the invention as claimed.

DETAILED DESCRIPTION OF THE PREFERRED EMBODIMENTS

Figure 1:
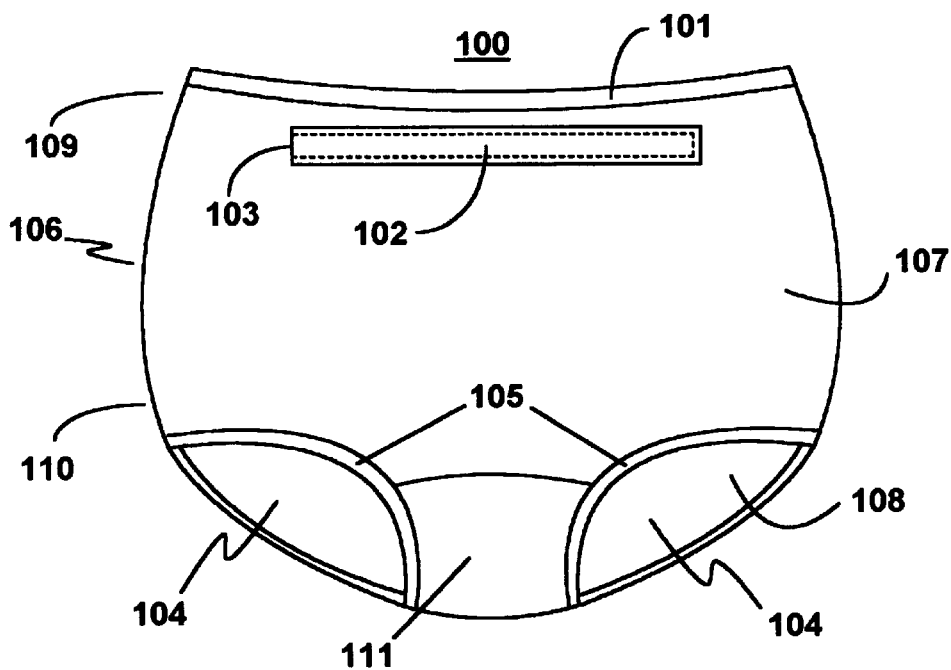
FIG. 1 is a front view of a preferred embodiment of the present invention showing the elongate pocket on a brief style undergarment.

The preferred embodiments of the present invention are illustrated in FIGS. 1–5. FIG. 1 shows a catheter undergarment 100 with a waistband 101, a fabric body 106, leg openings 104, and an elongate pocket 102. The fabric body 106 has a front 107, a back 108, a top 109, a bottom 110, and a crotch 111. The waistband 101 is secured to the top 109 of the fabric body 106. The leg openings 104 are reinforced around their edges by leg bands 105. The leg bands 105 are secured to the bottom 110 of the fabric body 106 and are separated by the crotch 111. The crotch 111 is located at the bottom 110 of the fabric body 106 and connects the front 107 with the back 108 of the fabric body 106 while also separating the leg bands 105. The elongate pocket 102 is preferably made of a material that is durable, washable, shrink proof, fray resistant, and easily workable such as cotton. The elongate pocket 102 may be installed anywhere on the undergarment 100, preferably on the outside of undergarment 100 on front 107 and located on waistband 101 or parallel to and just below waistband 101 as this location provides for easiest access to the wearer.

The elongate pocket 102 is secured to the fabric body 106 of the catheter undergarment 100 and has an open edge 103 adapted to receive a catheter or other specialized device. Elongate pocket 102 is preferably 8 or 9 inches long and 1 to 1.5 inches wide and may be secured by sewing, by use of hook and loop fasteners, buttons, or snaps, or heat-activated adhesive. Open edge 103 may be located at either end of the elongate pocket 102 to accommodate right or left handedness of the wearer. By locating the elongate pocket 102 parallel to and just below the waistband 101, the wearer of the catheter undergarment 100 does not appear to be wearing any specialized clothing and the elongate pocket 102 is effectively hidden beneath the wearer's clothes.

Figure 2:
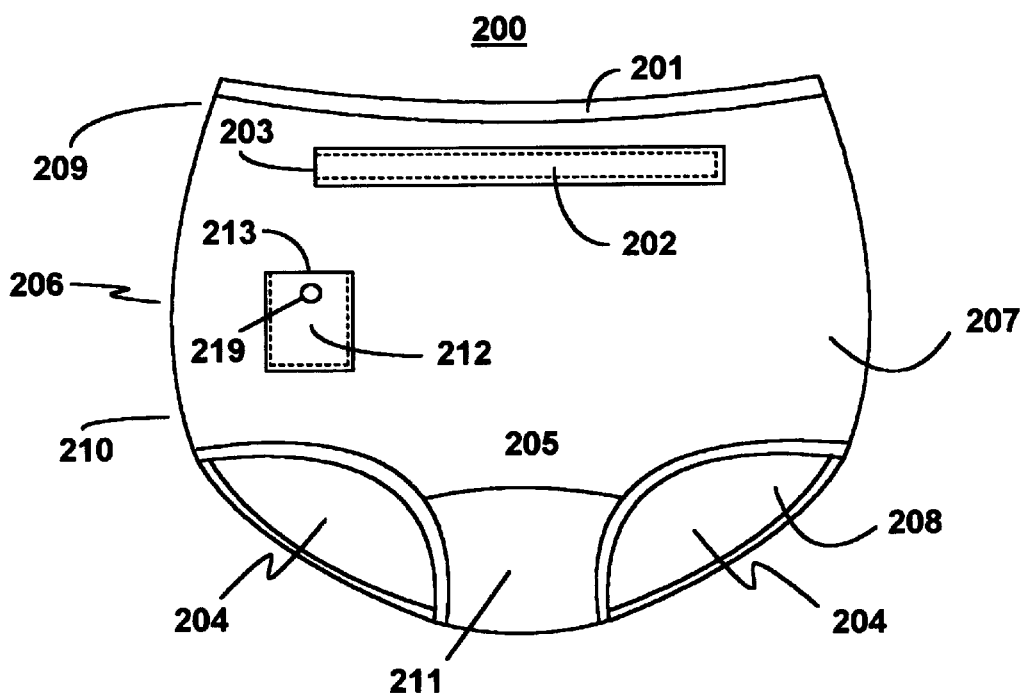
FIG. 2 is a front view of a preferred embodiment of the present invention showing the elongate pocket and a second pocket on a brief style undergarment.

FIG. 2 shows a catheter undergarment 100 as described in FIG. 1 in the form of a catheter brief 200. Catheter brief 200 is shown with a waistband 201, a fabric body 206, leg openings 204, and an elongate pocket 202. The fabric body 206 has a front 207, a back 208, a top 209, a bottom 210, and a crotch 211. The waistband 201 is secured to the top 209 of the fabric body 206. The leg openings 204 are reinforced around their edges by leg bands 205. The leg bands 205 are secured to the bottom 210 of the fabric body 206 and are separated by the crotch 211. The crotch 211 is located at the bottom 210 of the fabric body 206 and connects the front 207 with the back 208 of the fabric body 206 while also separating the leg bands 205. The elongate pocket 202 is shown installed parallel to and just below the waistband 201.

The elongate pocket 202 is secured to the fabric body 206 of the catheter brief 200 and has an open edge 203 adapted to receive a catheter or other specialized device. Open edge 203 may be located at either end of the elongate pocket 202 to accommodate right or left handedness of the wearer. Open edge 203 may be closed through the closing fastener 219.

A second pocket 212 is secured elsewhere on the fabric body 206 of the catheter brief 200. Second pocket 212 has an open edge 213 adapted to receive other specialized items for the user. Open edge 213 may also be closed by using the closing fastener 219. To reduce the risk of infection, persons requiring clean, intermittent self-catheterization and wearing catheter brief 200 may use second pocket 212 to store small antibacterial wipes. The antibacterial wipes stored in second pocket 212 provides the wearer with a convenient way to clean both their hands and the catheter prior to self-catheterization regardless of their surroundings.

Figure 3:
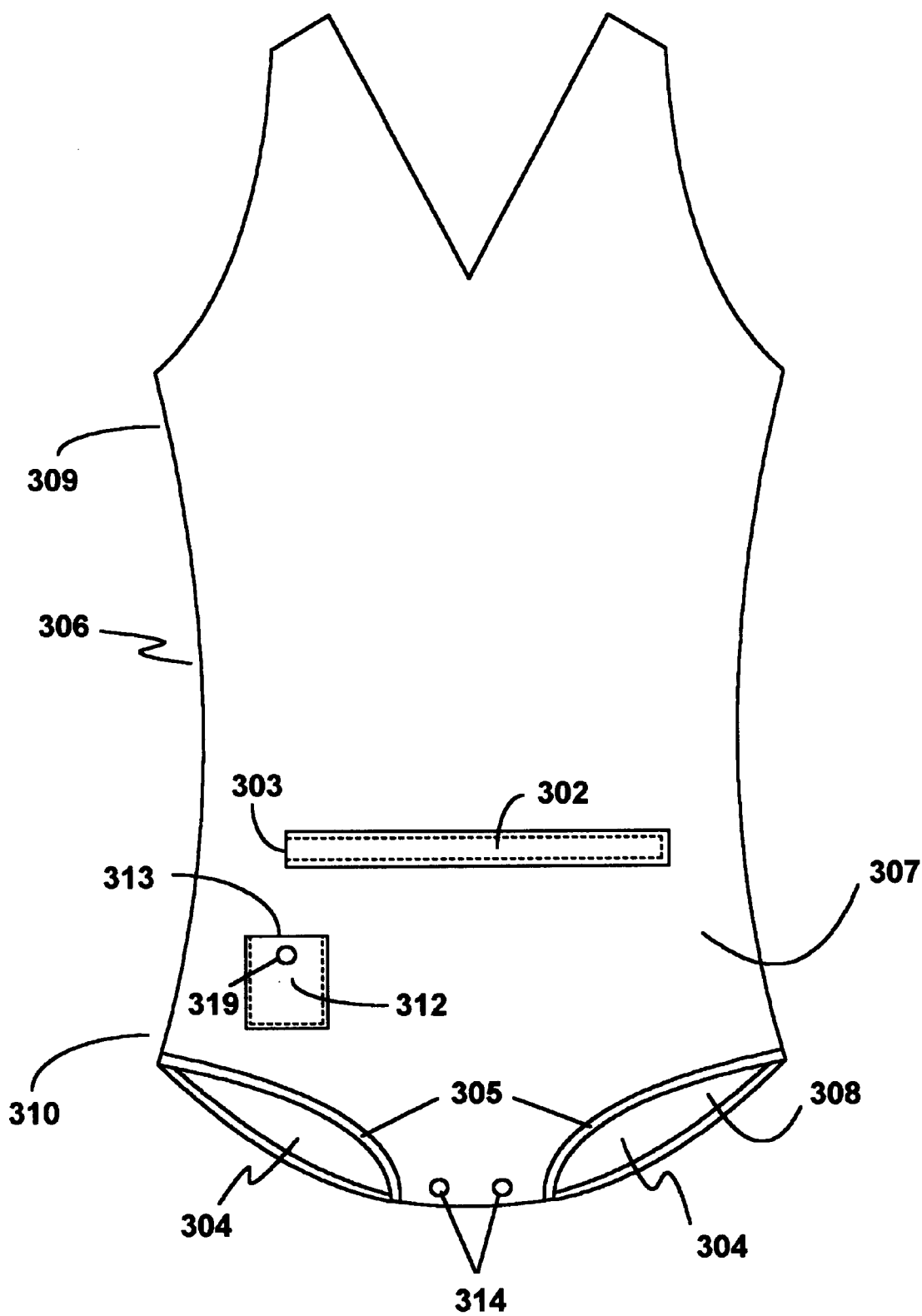
FIG. 3 is a front view of a preferred embodiment of the present invention showing the elongate pocket and a second pocket on a bodyshirt style undergarment.

FIG. 3 illustrates a second embodiment of the present invention, a catheter body shirt 300. The catheter body shirt 300 has a body shirt fabric body 306 with a top 309, bottom 310, back 308, and front 307. The catheter body shirt top 309 is fashioned to cover the torso of the wearer while the catheter body shirt bottom 310 terminates in a crotch 311. The catheter body shirt crotch 311 is equipped with at least one fastener 314 which connects the catheter body shirt back 308 with the catheter body shirt front 307 and provides a separation for the leg openings 304. The leg openings 304 are surrounded by leg bands 305 which help to ensure a snug fit and reinforce the leg openings 304. The catheter body shirt 300 as shown in FIG. 3 has both an elongate pocket 302 with an open edge 303 and a second pocket 312 with an open edge 313 attached to the catheter body shirt fabric body 306. Both open edge 303 and open edge 313 can be closed by engaging closing fastener 319.

Figure 4:
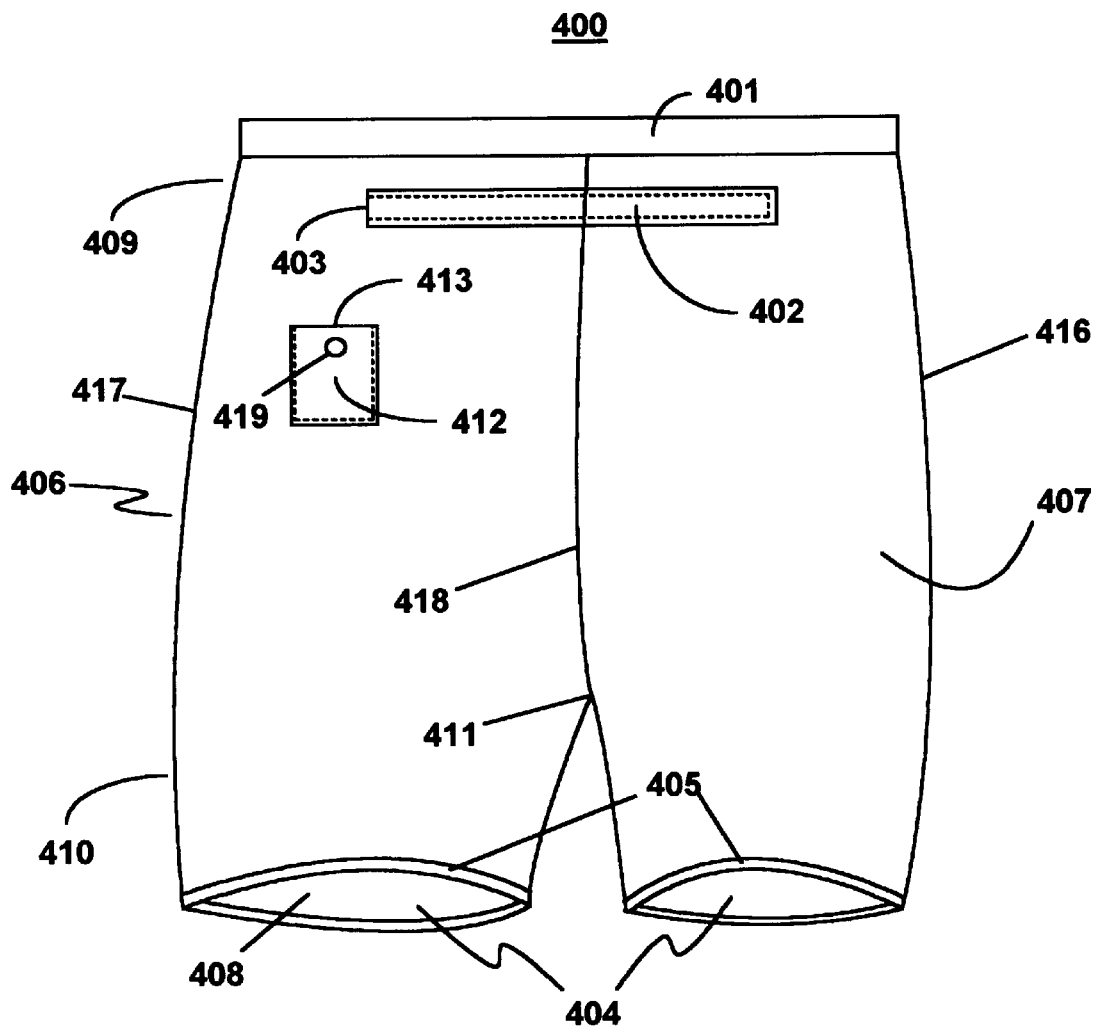
FIG. 4 is a front view of another preferred embodiment of the present invention showing the elongate pocket and a second pocket on a boxer shorts style undergarment.

FIG. 4 illustrates the present invention placed on a third type of undergarment, catheter boxer shorts 400. The catheter boxer shorts 400 comprises a boxer shorts fabric body 406 with a left side 416, a right side 417, a top 409, and a bottom 410. The boxer shorts fabric body left side 416 and boxer shorts fabric body right side 417 are connected with a seam 418. The boxer shorts fabric body top 409 is bordered on its outermost edge by a waistband 401. The boxer shorts fabric body bottom 410 terminates at its midpoint in a catheter boxer shorts crotch 411 which separates pant legs 415 that extend past the catheter boxer shorts fabric body bottom 410 and the catheter boxer shorts crotch 411. The pant legs 415 each have a leg opening 404. The catheter boxer shorts 400 is equipped with an elongate pocket 402 with an open edge 403. There is also a second pocket 412 with an open edge 413. Open edge 413, as illustrated in FIG. 4, can be closed by operating closing fastener 419.

Figure 5:
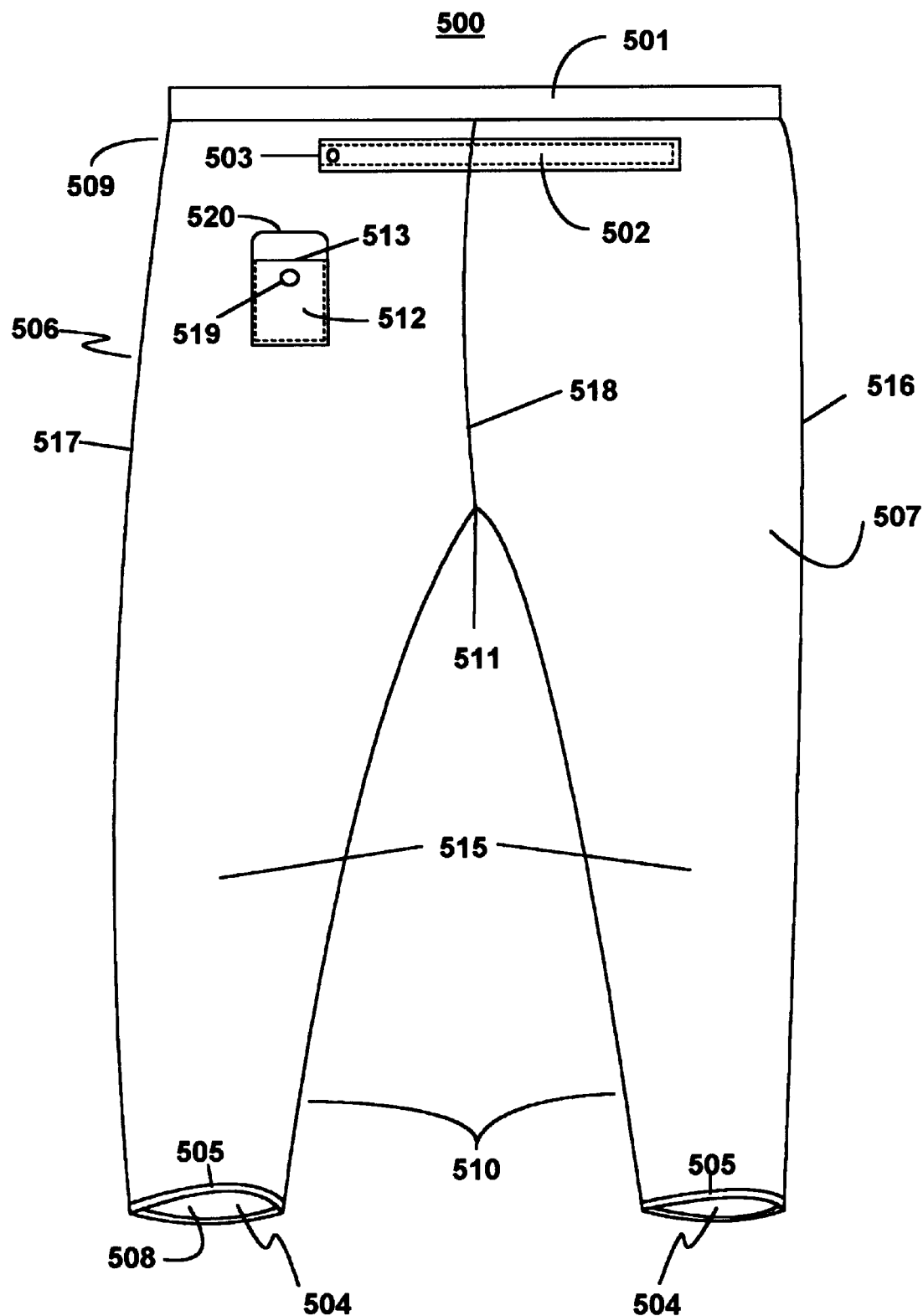
FIG. 5 is a front view of another preferred embodiment of the present invention showing the elongate pocket and a second pocket on a long underwear style undergarment.

A full length catheter undergarment 500 is shown in FIG. 5. This full length catheter undergarment 500 has a full length catheter undergarment fabric body 506 with a top 509, a bottom 510, a left side 516, and a right side 517. The full length catheter undergarment top 509 terminates at a waistband 501. The full length catheter undergarment bottom 510 terminates at a crotch 511 at its midpoint and in long pant legs 515 on both the left side 516 and the right 517 side, respectively. The long pant legs 515 both have leg openings 504 which allow the wearer to insert his legs and keep a substantial portion of them covered. The full length catheter undergarment 500 is equipped with both an elongate pocket 502 with an open edge 503 and a second pocket 512 with an open edge 513. Open edge 513 may be covered by covering flap 520 which can be pulled down over open edge 513 after insertion of something into the second pocket 512 to prevent or reduce the possibility of losing anything through the open edge 513. Alternatively, both the elongate pocket 502 and the second pocket 512 may be equipped with a closing fastener 519 that closes the open edge of the elongate pocket 502 or the open edge of the second pocket 513. A seam 518 separates the full length catheter undergarment right side 517 from the full length catheter undergarment left side 516 in the full length catheter undergarment 500.

While this invention is susceptible of embodiment in many different forms, there is shown in the drawings and described herein in detail preferred embodiments of the invention with the understanding that the present disclosure is to be considered as an exemplification of the principles of the invention and is not intended to limit the broad aspect of the invention to the embodiments illustrated.

What is claimed is:

1. An adaptive undergarment comprising:
    a fabric body having a back, a front, a top, a bottom and a crotch;
    a waistband secured to said top of said fabric body;
    leg openings located at said bottom of said fabric body and separated by said crotch; and
    an elongate pocket having side edges, elongated top and bottom edges and an open edge and secured to said fabric body, wherein said open edge is positioned on one of said side edges and wherein said elongate pocket is of sufficient size for storing at least one catheter used for intermittent self-catheterization.

2. The adaptive garment as claimed in claim 1, wherein said elongate pocket is parallel to and affixed onto said front of said fabric body below said waistband.

3. The adaptive undergarment as claimed in claim 1, wherein said elongate pocket is parallel to and on said waistband.

4. The adaptive undergarment as claimed in claim 1, further comprising at least one second pocket secured to said fabric body below said elongate pocket, said at least one second pocket having one open edge.

5. The adaptive undergarment as claimed in claim 1, further comprising a closing fastener at said open edge of said elongate pocket.

6. The adaptive undergarment as claimed in claim 1, further comprising a covering flap extending over said open edge of said elongate pocket.

7. The adaptive undergarment as claimed in claim 4 wherein said second pocket is of sufficient size for storing at least one antibacterial wipe.

8. The adaptive undergarment as claimed in claim 1 wherein said fabric body bottom is adapted to cover a portion of the wearer's legs.

9. An adaptive undergarment kit for adapting at least one undergarment having a waistline comprising:
    at least one elongate pocket having side edges and an elongate pocket perimeter for attaching to said at least one undergarment in the vicinity of said waistline and substantially parallel to said at least one undergarment, and has an open portion positioned on one of said side edges; and
    a securing device for attaching said pocket to said at least one undergarment.

10. The adaptive undergarment kit as claimed in claim 9 further comprising at least one second pocket having a second pocket perimeter wherein said second pocket perimeter has an open portion.

11. The adaptive undergarment kit as claimed in claim 9 further comprising a closing fastener on said open portion of said at least one elongate pocket perimeter.

12. The adaptive undergarment kit as claimed in claim 10 further comprising a closing fastener on said open portion of said second pocket perimeter.

13. The adaptive undergarment kit as claimed in claim 9 further comprising a covering flap over said open portion of said at least one elongate pocket perimeter.

14. The adaptive undergarment kit as claimed in claim 9 wherein said securing device is selected from the group consisting of glue, heat activated adhesive, thread, epoxy, hook and loop fasteners, snaps, buttons, and string.

15. The adaptive undergarment kit as claimed in claim 14 wherein said securing device is predisposed on the majority of the perimeter of said pocket.

16. The adaptive undergarment as claimed in claim 4 further comprising a closing fastener on said open edge of said second pocket.

17. An adaptive body undergarment adapted for persons requiring intermittent self-catheterization, said adaptive body undergarment comprising:
    a fabric body having a back, a front, a top, a bottom, a waistline and a crotch, wherein said crotch further contains at least one fastener to removably attach said front to said back at said crotch, and wherein said top is adapted to fit over at least one shoulder and cover a substantial portion of the wearer's torso;

leg openings located at said bottom of said fabric body and separated by said crotch; and an elongate pocket having side edges, elongated top and bottom edges and an open edge and secured to said fabric body at about said waistline, wherein said open edge is positioned on one of said side edges and wherein said elongate pocket is of sufficient size for storing at least one elongate catheter used for intermittent self-catheterization.

18. The adaptive body undergarment as claimed in claim 17 further comprising at least one additional pocket secured to said fabric body, said at least one additional pocket having an open top edge.

19. The adaptive body undergarment as claimed in claim 17 further comprising a closing fastener at said open edge of said elongate pocket.

20. The adaptive body undergarment as claimed in claim 17 further comprising a covering flap extending over said open edge of said elongate pocket.

* * * * *